(12) United States Patent
Albitar

(10) Patent No.: US 7,569,353 B2
(45) Date of Patent: Aug. 4, 2009

(54) MYELOPEROXIDASE DETECTION IN DIAGNOSIS AND PROGNOSIS OF HEMATOPOIETIC DISORDERS

(75) Inventor: Maher Albitar, Coto De Caza, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 457 days.

(21) Appl. No.: 10/982,534

(22) Filed: Nov. 4, 2004

(65) Prior Publication Data

US 2006/0094066 A1     May 4, 2006

(51) Int. Cl.
*G01N 33/53* (2006.01)

(52) U.S. Cl. .................. 435/7.1; 435/7.2; 435/7.91; 435/7.92

(58) Field of Classification Search ............. 435/4, 435/7.1, 7.91, 7.92, 7.93, 25, 7.2; 436/8, 436/63
See application file for complete search history.

(56) References Cited

U.S. PATENT DOCUMENTS

| | | | |
|---|---|---|---|
| 4,614,513 | A | 9/1986 | Bensinger |
| 4,637,880 | A | 1/1987 | Halbert |
| 4,685,900 | A | 8/1987 | Honard et al. |
| 5,200,319 | A | 4/1993 | Arnaout et al. |
| 6,569,112 | B2 | 5/2003 | Strahilevitz |
| 6,599,713 | B1 | 7/2003 | Hatanaka et al. |
| 2006/0035308 | A1* | 2/2006 | Yuan et al. ............ 435/25 |

OTHER PUBLICATIONS

Oberg et al. (Eur. J Haematol 1987 vol. 38: 148-155).*
Malmquist et al. (Scand. J. Haemat. 1972, vol. 9, p. 311-317).*
Giles et. al., A prognostic model for survival in chronic lymphocytic leukemia based on p53 expression. British Journal of Hemotology, 121:578-585.
Kamik et al., Use of polyclonal anti-myeloperoxidase antibody in myeloid lineage determination. Indian J Med Res. 100: 272-6, Dec. 1994.
Matsuo et al., The percentage of myeloperoxidase-positive blast cells is a strong independent prognostic factor in acute myeloid leukemia, even in the patients with normal karyotype. Leukemia, 17:1538-1543, 2003.

* cited by examiner

*Primary Examiner*—Mark L Shibuya
*Assistant Examiner*—Jacob Cheu
(74) *Attorney, Agent, or Firm*—Foley and Lardner LLP

(57) ABSTRACT

The present invention relates to the diagnosis of hematopoietic disorders and to determining the prognosis of patients affected by such disorders. The methods generally comprise determining a level of myeloperoxidase in a body fluid sample from the individual and using the level as a factor for diagnosing the disorder in the mammal or as a factor for determining the prognosis of a patient diagnosed with such a disorder. Myelodysplastic syndrome, acute myeloid leukemia and chronic myeloid leukemia are exemplary disorders. Also provided are method of cancer therapy involving reducing the level of myeloperoxidase in the body fluid of the individual.

14 Claims, 3 Drawing Sheets

MPO in chronic and ACC/BC CML

P=0.03

Patients with CML in Accelerated/Blastic phase

P=0.04

MYELOPEROXIDASE DETECTION IN DIAGNOSIS AND PROGNOSIS OF HEMATOPOIETIC DISORDERS

FIELD OF THE INVENTION

The invention relates to detection of myeloperoxidase and its use in the diagnosis and prognosis of hematopoietic disorders.

BACKGROUND OF THE INVENTION

The following description of the background of the invention is provided simply as an aid in understanding the invention and is not admitted to describe or constitute prior art to the invention.

Leukemia is a malignant disease of the blood-forming organs which involves the distorted proliferation and development of leukocytes and their precursors in bone marrow and blood. Acute myeloid leukemia (AML) is caused by a malignant event occurring in an immature myeloid hematopoietic precursor resulting in cells that proliferate excessively and fail to differentiate normally. In AML patients immature myeloid cells rapidly accumulate and progressively replace the bone marrow leading to diminished production of normal red blood cells, white blood cells and platelets. If untreated, AML patients usually die within months following diagnosis. A form of preleukemia related to AML is known as myelodysplastic syndrome (MDS). MDS encompasses a heterogeneous group of bone marrow disorders characterized by a hypercellular bone marrow with peripheral cytopenia, and propensity to progress to acute myeloid leukemia.

Chronic myloid leukemia (CML) is a myeloproliferative disorder characterized by increased proliferation of the granulocytic cell line without the loss of the capacity to differentiate. Consequently, the peripheral blood cell profile of CML patients shows an increased number of granulocytes and their immature precursors. CML accounts for approximately 20% of all adult leukemias.

The progression of CML disease can be classified into three phases, an initial chronic phase where the disease is often indolent, an accelerated phase (ACC) that may last 6 to 18 months and a blast crisis phase where survival is usually limited to about 3 to 6 months. Before effective treatments were available, CML patients survived on average two years after being diagnosed.

Myeloperoxidase (MPO) is a hallmark enzyme of the myeloid lineage and is found in the granules of myeloid precursors and their leukemic cell counterparts. Determination of the percentage of MPO expressing blast cells has been used as a factor for the diagnosis of AML. A recent publication reported that the percentage of MPO-positive blast cells may be a prognostic factor for AML patients (Matsuo et al., *Leukemia*, (2003) 17:1538-1543).

Improved methods are needed for diagnosing leukemia and for determining the prognosis of leukemia patients.

SUMMARY OF THE INVENTION

Provided are methods for diagnosing a hematological disorder by detecting the level of myeloperoxidase in a body fluid sample of a mammal. The hematological disorder may be a leukemia such as AML or CML, or a hematological disorder such as MDS. A diagnosis can be accomplished in some cases by providing the MPO level to a medical practitioner who uses it as a factor in making the diagnosis. In some aspects, a level of MPO that is greater than for a comparable sample from normal individuals is indicative of a diagnosis of cancer. In some aspects, an MPO level greater than 20 ng/mL is a factor related to diagnosis. In a preferred embodiment, the mammal is a human. Preferably, the body fluid sample does not contain cells. Preferably, the method does not include a step of lysing cells that may be present in the body fluid sample.

Also provided are methods for determining the prognosis of a patient with an abnormal level of circulating blood cells or a patient diagnosed with a hematological disorder. In one aspect the method includes determining a level of MPO in a body fluid sample from the patient and correlating the MPO level to a clinical outcome for the disease. In this approach, higher levels of myeloperoxidase correlate with worse prognosis. The hematological disorder may be a leukemia such as AML or CML, or a hematological disorder such as MDS. A prognosis can be accomplished in some cases by providing the MPO level to a medical practitioner who uses it as a factor in making the prognosis. In certain embodiments prognosis is expressed in terms of survival, with a favorable prognosis indicating that the patient is expected to survive longer than a patient with an unfavorable prognosis. In other embodiments, the prognosis is expressed in terms of complete remission duration (CRD). In the latter case, the method is predictive of CRD in an MDS or AML patient undergoing treatment wherein higher than normal MPO levels are indicators for a prediction of a shorter CRD. In some aspects, an MPO level greater than 20 ng/mL is a factor related to prognosis. In a preferred embodiment, the patient is a human. Preferably, the body fluid sample does not contain cells. Preferably, the method does not include a step of lysing cells that may be present in the body fluid sample.

The invention also provides methods for predicting whether a patient is expected to respond to treatment. In certain aspects the method involves determining a level of MPO in a body fluid sample from the patient using the MPO level as a factor for predicting the whether the patient will respond to treatment. In some embodiments the patient is a myeloid leukemia patient such as a CML patient or has an MPO containing hematological disorder. In some embodiments, the treatment involves administering Gleevec to the patient. In a preferred embodiment, the patient is diagnosed with CML and treated with Gleevec. In a preferred embodiment, the patient is a human. Preferably, the body fluid sample does not contain cells. Preferably, the method does not include a step of lysing cells that may be present in the body fluid sample.

Methods are also provided for determining the French-American-British (FAB) concentration of an AML patient. In certain aspects the method includes determining a level of MPO in a body fluid sample from the patient using the MPO level as an indicator of the FAB classification of the AML patient. In certain embodiments, a level of MPO that is greater than for a comparable sample from normal individuals is indicative that the patient is not M0 or M6. In a preferred embodiment, the patient is a human. Preferably, the body fluid sample does not contain cells. Preferably, the method does not include a step of lysing cells that may be present in the body fluid sample.

Further provided are methods of treating an MDS or AML patient with abnormal levels of circulating plasma MPO by reducing the level of circulating MPO in the patient. The level of circulating MPO may be reduced by, for example, extracorporeal affinity absorption from plasma. Affinity absorption may be done using an anti-MPO antibody. This method of treatment may have any of various clinical benefits including extending survival and extending the time for disease free remission.

The term "patient," as used herein refers to an individual who is under the care of a medical practitioner, an individual who is ill, or an individual who is affected with a disease or disorder. Preferably, patients of the present invention are humans; however, animals that are ill, under veterinarian care or affected by a disease or disorder may also be patients as used herein.

The term "medical practitioner" as used herein refers to a person that practices medicine. Non-limiting examples of medical practitioners of the invention include nurses, physicians and surgeons. A preferred medical practitioner of the present invention is a physician. In certain embodiments a medical practitioner may be any person that is capable of, or qualified to, diagnose a disease or disorder in a mammal; is capable of, or qualified to, determine the prognosis of a patient.

The term "hematological disorder" as used herein means a disorder of a bone marrow derived cell type such as a white blood cell. A hematologic disorder is preferably manifest by abnormal cell division resulting in an abnormal level of a particular hematological cell population. The abnormal cell division underlying a hematological disorder is preferably inherent in the cells and not a normal physiological response to infection or inflammation. A leukemia is a type of hematological disorder. Infection or acute inflammation resulting in a transient spike in circulating white blood cells is preferably not included within the meaning of a hematologic disorder.

White blood cells include granulocytes, macrophages and lymphocytes, and the like. A myeloid cell is a type of white blood cell. Examples of hematological disorders which involve cells of myeloid lineage include MDS, and leukemias such as AML and CML. Cells of the myeloid lineage may be characterized in having enzyme containing storage granules. The phrase "an abnormal level of circulating blood cells" encompasses hematological disorders as well as cell inflammation and infection, however, inflammation due to cardiovascular abnormalities is excluded from this group.

The term "MDS" patient as used herein refers to a patient diagnosed with MDS. One of ordinary skill in the art is capable of diagnosing MDS using suitable diagnostic criteria. Likewise, the term "AML patient" and CML patient refers to a patient diagnosed with AML or CML, respectively.

The term "body fluid" or "bodily fluid" as used herein refers to any fluid from the body of an animal. Examples of body fluids include but are not limited to plasma, serum, blood, lymphatic fluid, cerebrospinal fluid, synovial fluid, urine, saliva, mucous, phlegm and sputum. Plasma and serum are preferred body fluids of the present invention. A body fluid sample of the present invention may be collected by any suitable method. The body fluid sample may be used immediately or may be stored for later use. Any suitable storage method known in the art may be used to store the body fluid sample; for example the sample may be frozen at about −20° C. to about −70° C.

A body fluid may include cells resident in the fluid. Alternatively, a body fluid may be used with any cells removed. Cells in a body fluid also may be lysed prior to testing the body fluid. In such case, the amount of MPO represents the amount in the initial liquid portion of the body fluid sample and the amount present within cells that were lysed. Methods of lysing blood to release myeloperoxidase are described in U.S. Pat. No. 6,599,713 (Hatanaka et al.). Preferably, only the liquid portion of an initial body fluid sample is tested for an MPO level.

The term "comparable sample" means the same type of sample (e.g. serum in both cases) or a sample that is essentially similar with respect to the amount of MPO that would be present in the sample. For example, the liquid portion of a blood sample and plasma are comparable samples.

As used herein the term "circulating" or "circulating levels" refers to the amount of an analyte, such as MPO, in the blood of a mammal, preferably in the liquid portion of the blood.

The term "immunoassay" as used herein refers to any assay that utilizes conventional immunological techniques, for example, radioimmunoassay (RIA), immunoradiometric assay, enzyme-linked immunosorbent assay (ELISA), enzyme labelled immunometric assay, fluorescent labelled immunoassay, luminescent labelled immunoassay, immunoprecipitation assay or particle and agglutination immunoassay. See also Ray Edwards, Immunoassay, An introduction, 1985, William Heineman Medical Books LTD., and the content is hereby incorporated into the specification by reference.

The term "diagnose" as used herein refers to the act or process of identifying or determining a disease or condition in a mammal or the cause of a disease or condition by the evaluation of the signs and symptoms of the disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to said particular disease; i.e. there may be differential diagnoses that can be inferred from a diagnostic factor or symptom. Likewise, there may be instances where a factor or symptom that is indicative of a particular disease is present in an individual that does not have the particular disease.

The term "using" as used herein in reference to diagnostic factors, refers to comparing the presence or amount of the diagnostic factor (e.g., MPO) in a patient to the presence or amount of the factor in persons known to suffer from, or known to be at risk of, a given condition; or in persons known to be free of a given condition. Likewise, the term using as used herein in reference to prognostic factors, refers to comparing the presence or amount of the factor in a patient diagnosed with a particular disorder, to its presence or amount in patients diagnosed with the same disorder of whom the outcome of the disorder is known. In certain embodiments of the invention, a threshold level of MPO can be established, and the level of MPO in a patient sample can simply be compared to the threshold level.

The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease.

The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average, that a patient can expect to survive as a result of a condition or disease. The prognosis of a patient may be considered as an expression of relativism, with many factors effecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense a "favorable prognosis" an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, if a prognosis is that a patient has a 50% probability of being cured of a particular cancer after treatment, while the average patient with the same cancer has only a 25% probability of being cured, then that patient exhibits a positive prognosis. A positive prognosis may be indicated by, for example, chemical destruction of a tumor vasculature. Alternatively, diagnosis of a benign tumor would lead to a positive prognosis if it is distinguished over a cancerous tumor.

A prognosis is often determined by examining one or more prognostic factors or indicators. These are markers, such as an MPO level, the presence or amount of which in a patient (or a sample obtained from the patient) signal a probability that a given course or outcome will occur. The skilled artisan will understand that associating a prognostic indicator with a predisposition to an adverse outcome may involve statistical analysis.

Additionally, a change in factor concentration from a baseline level may be reflective of a patient prognosis, and the degree of change in marker level may be related to the severity of adverse events. Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Exemplary statistical tests for associating a prognostic indicator with a predisposition to an adverse outcome are described hereinafter.

Moreover, multiple determinations of MPO levels can be made, and a temporal change in the marker can be used to determine a diagnosis or prognosis. For example, comparative measurements are made of the MPO in a patient at multiple time points, and a comparison of two or more MPO values may be indicative of a particular diagnosis or prognosis.

The term "about" as used herein in reference to quantitative measurements, refers to the indicated value plus or minus 10%.

The term extracorporeal affinity absorption refers to the process whereby blood from an individual is separated continuously into a plasma fraction and a cell fraction, the plasma fraction then contacts an affinity column which removes a particular analyte from the plasma, with the processed plasma fraction and blood cell being recombined and returned to the individual.

DETAILED DESCRIPTION OF THE INVENTION

Figure 1:
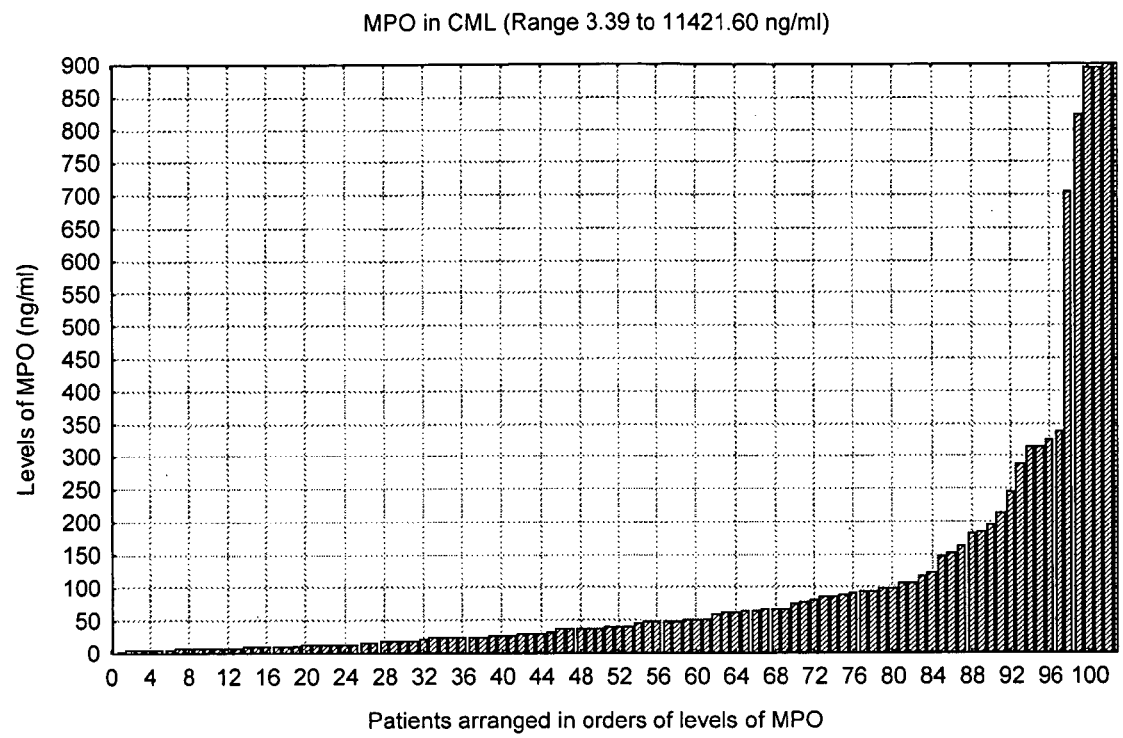
FIG. 1 shows the distribution of MPO levels in patients diagnosed with CML.

The present invention relates to the determination of MPO levels in a body fluid sample of a mammal and using said MPO levels as a factor for diagnosing a hematological disorder (e.g., myeloid disorder) in the mammal. In this approach, a myeloperoxidase level that is higher than for a comparable sample from normal individuals is a factor favoring diagnosis of a hematological disorder while a myeloperoxidase level that is equal to or lower than for a comparable sample from normal individuals is a factor against diagnosis of a hematological disorder.

The present invention also relates to the determination of MPO levels in a body fluid sample of a mammal and using the MPO levels as a factor for predicting the outcome (i.e., prognosis) of a patient with an abnormal level of circulating blood cells. In this approach, the MPO level is correlated with a clinical outcome for the disease. Higher levels of myeloperoxidase correlate with worsening prognosis. The outcome or prognosis can vary and may include predicting the complete remission duration of a patient undergoing treatment for the disorder, predicting whether a patient affected with the disorder will respond to treatment, and/or predicting the FAB classification of a patient affected with a myeloid disorder.

The term "elevated levels" or "higher levels" as used herein refers to levels of an analyte, such as MPO, that are higher than what would normally be observed in a comparable body fluid sample from control or normal subjects. In some embodiments of the invention "control levels" (i.e. normal levels) refer to a range of MPO levels that would be normally be expected to be observed in a mammal that does not have a hematological disorder and "elevated levels" refer to MPO levels that are above the range of control levels. The ranges accepted as "elevated levels" or "control levels" are dependant on a number of factors. For example, one laboratory may routinely determine absolute levels of an analyte in a sample that are different than the absolute levels obtained for the same sample by another laboratory. Also, different assay methods may achieve different value ranges. Value ranges may also differ in various body fluids or by different treatments of the body fluids. One of ordinary skill in the art is capable of considering the relevant factors and establishing appropriate reference ranges for "control values" and "elevated values" of the present invention. For example, a series of samples from control subjects and subjects diagnosed with hematological disorders can be used to establish ranges that are "normal" or "control" levels and ranges that are "elevated" or "higher" than the control range.

In some embodiments of the present invention, control levels of MPO in plasma with EDTA as an anticoagulant are lower than about 100 ng/mL or lower than about 30 ng/mL, or lower than about 20 ng/mL; control levels of MPO in plasma with heparin as the anticoagulant are lower than 1,000 ng/mL or lower than 100 ng/mL or lower than about 35 ng/mL; control levels of MPO in serum are lower than 1,000 ng/mL or lower than 100 ng/mL or lower than about 45 ng/mL. In those embodiments, values above the control would be indicative that the mammal may have MDS, AML or CML or other hematological disorder. In some embodiments of the present invention, elevated MPO levels are levels of MPO higher than about 20 ng/mL, or higher than about 30 ng/mL, or higher than about 40 ng/mL, or higher than about 100 ng/mL in plasma with EDTA used as an anticoagulant. In other embodiments elevated MPO levels are levels of MPO higher than about 36 ng/mL, or higher than about 50 ng/mL, or higher than about 100 ng/mL, or higher than about 1,000 ng/mL in plasma with heparin used as an anticoagulant. In yet other embodiments, elevated MPO levels are levels of MPO higher than about 45 ng/mL in serum. In other embodiments, values of MPO may be used to distinguish CML from AML or MDS. In these embodiments very high levels of MPO may indicate CML.

Often, diagnostic assays are directed by a medical practitioner treating a patient, the diagnostic assays are performed by a technician who reports the results of the assay to the medical practitioner, and the medical practitioner uses the values from the assays as criteria for diagnosing the patient. Accordingly, the component steps of the method of the present invention may be performed by more than one person. In certain embodiments, the MPO level in a body fluid is used as a factor to diagnose a hematological disorder such as MDS, AML and CML. In related embodiments the MPO level in a body fluid of an individual with an abnormal level of circulating blood cells is used to determine the prognosis of the individual. In the above embodiments, the medical practitioner receiving the MPO level value may be provided with ranges indicating normal or control levels of MPO and levels that would be considered elevated for use in determining diagnosis or prognosis. A skilled artisan is capable of diagnosing said myeloid disorder using suitable diagnostic criteria. It was found that patients diagnosed with MDS or AML that had higher levels of MPO had significantly worse outcomes than MDS or AML patients with lower MPO levels.

Prognosis may be a prediction of the likelihood that a patient will survive for a particular period of time, or said prognosis is a prediction of how long a patient may live, or the prognosis is the likelihood that a patent will recover from a disease or disorder. There are many ways that prognosis can be expressed. For example prognosis can be expressed in terms of complete remission rates (CR), overall survival (OS) which is the amount of time from entry to death, disease-free survival (DFS) which is the amount of time from CR to relapse or death.

In certain embodiments high levels of MPO are used as indicators of an unfavorable prognosis. According to the method, the determination of prognosis can be performed by comparing the measured MPO levels to levels known to corresponding with favorable or unfavorable outcomes. The absolute MPO values obtained in the detection step depend on an number of factors, including but not limited to the laboratory performing the assays, the assay methods used, the type of body fluid sample used and the type of myeloid disease a patient is afflicted with. According to the method, values can be collected from a series of patients with myeloid disorders to determine appropriate reference ranges of MPO for the a particular myeloid disorder. One of ordinary skill in the art is capable of performing a retrospective study that compares the determined MPO levels to the observed outcome of the patients and establishing ranges of MPO levels that can be used to designate the prognosis of the patients with a particular myeloid disorder. For example, MPO levels in the lowest range would be indicative of a more favorable prognosis, MPO levels in intermediate ranges indicative of an intermediate prognosis and MPO levels in the highest ranges would be indicative of an unfavorable prognosis. Thus, in this aspect the term "elevated levels" refers to levels of MPO that are within higher ranges for a patient with a particular myeloid disease. For example MDS patients with "high" or "elevated" MPO levels have levels of MPO that are higher than that observed in many NDS patients. In certain embodiments, "high" or "elevated" MPO levels for a patient with a particular myeloid disease refers to levels that are above the median values for patients with that disorder, or to MPO levels that are in the upper 40% of patients with the disorder, or to MPO levels that are in the upper 20% of patients with the disorder, or to MPO levels that are in the upper 10% of patients with the disorder, or to MPO levels that are in the upper 5% of patients with the disorder.

Because the MPO levels in a body fluid from a patient relate to the prognosis of a patient in a continuous fashion, the determination of prognosis can be performed using statistical analyses to relate the determined MPO level to the prognosis of the patient. A skilled artisan is capable of designing appropriate statistical methods. For example the methods of the present invention may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses.

In certain embodiments, the prognosis of AML or MDS patients can be correlated to the clinical outcome of the disease using the MPO levels and other clinical factors. Simple algorithms have been described and are readily adapted to this end. The approach by Giles et. al., *British Journal of Hemotology*, 121:578-585, hereby incorporated as reference, is exemplary. As in Giles et al., associations between categorical variables (e.g., MPO level and clinical characteristics) can be assessed via crosstabulation and Fisher's exact test. Unadjusted survival probabilities can be estimated using the method of Kaplan and Meier. The Cox proportional hazards regression model also can be used to assess the ability of patient characteristics (such as MPO levels) to predict survival, with 'goodness of fit' assessed by the Grambsch-Themeau test, Schoenfeld residual plots, martingale residual plots and likelihood ratio statistics (see Grambsch, 1995; Grambsch et al, 1995). In some embodiments this approach can be adapted as a simple computer program that can be used with personal computers or personal digital assistants (PDA). The prediction of patients' survival time in based on their MPO levels can be performed via the use of a visual basic for applications (VBA) computer program developed within Microsoft® excel. The core construction and analysis may be based on the Cox proportional hazard models. The VBA application can be developed by obtaining a base hazard rate and parameter estimates. These statistical analyses can be performed using a statistical program such as the SAS® proportional hazards regression, PHREG, procedure. Estimates can then be used to obtain probabilities of surviving from one to 24 months given the patient's covariates. The program can make use of estimated probabilities to create a graphical representation of a given patient's predicted survival curve. In certain embodiments, the program also provides 6-month, 1-year and 18-month survival probabilities. A graphical interface can be used to input patient characteristics in a user-friendly manner.

In some embodiments of the invention, multiple prognostic factors, including MPO levels, are considered when determining the prognosis of a patient. For example, the prognosis of a MDS or AML patient may be determined based on MPO levels and one or more prognostic factors selected from the group consisting of cytogenetics, performance status, AHD (antecedent hematological disease), age, and diagnosis (MDS v. AML). In certain embodiments, other prognostic factors may be combined with the MPO level in the algorithm to determine prognosis with greater accuracy.

In certain aspects of the invention, methods are provided to treat a patient diagnosed with MDS or AML, the method comprising the use of a clinical regimen that lowers the level of non-cell associated MPO circulating in the patient. In some embodiments, the method of treatment may extend survival time. In another embodiments, the method of treatment may extend the time to remission. In yet other embodiments, the methods of treatment may improve the expected course of disease. Preferably levels of MPO in MDS or AML patients are lowered using clinical regimens to extend the survival time of the patient.

Extracorporeal immunoabsorption methods can be used to lower the level of MPO circulating in a patient. Devices and methods involving extracorporeal immunoadsorption of for the selective removal of antigens from the liquid portion of blood (i.e., plasma) are well known in the art, e.g., see U.S. Pat. Nos. 4,614,513, 4,637,880 4,685,900 and 6,569,112. Such devices and methods can be adapted such that anti-MPO antibodies are used to remove circulating MPO from a patient's blood, thus resulting in lower levels of circulating non-cell associated MPO. MPO antibodies and methods for generating anti-MPO antibodies are well known in the art, see for example Kamik M P, et al. Indian J Med Res. 1994 December;100:272-6 and U.S. Pat. No. 5,200,319. In another approach, the level of MPO may be reduced functionally speaking by administering an agent which antagonizes the enzymatic activity of MPO. One skilled in the art is capable of designing such a small molecule antagonist (e.g. a peptide or organic molecule) to achieve this end.

In other aspects of the invention, methods are provided for predicting the complete remission duration of a hematopoietic disorder patient undergoing treatment, the method comprising determining the level of MPO in a body fluid sample from the patient and using the MPO level as a factor for predicting the complete remission duration of the patient. In preferred embodiments said hematopoietic disorder is a myeloid disorder such as MDS, AML, or CML. More preferably, the myeloid disorder is an MDS or AML disorder. The "treatment" can be any therapeutic regimen employed for the purpose of improving the condition of the patient. For example, the treatment may be bone marrow transplant, chemotherapy, radiation therapy or the like. In some embodiments the treatment can be the administration of cytosine arabinoside (ara-C) with idarubicin. In preferred embodiments higher levels of MPO are used as indicators that the complete remission duration will be shorter than patients with lower levels of MPO. In a preferred embodiment an MPO level greater than about 9.2 ng/mL in an MDS or AML patient is indicates a prediction of a shorter complete remission duration than patients with MPO levels greater then about 9.2 ng/mL.

In other aspects of the invention methods are provided for predicting the whether a hematopoietic disorder patient will respond to treatment, the method comprising determining the level of MPO in a body fluid sample from the patient and using the MPO level as a factor for predicting whether said patient will be a responder or a non-responder to treatment. In preferred embodiments said hematopoietic disorder is a myeloid disorder. More preferably, the myeloid disorder is CML. The treatment is preferably Gleevec. In preferred embodiments high MPO levels are indicative that a patient will be a non-responder to treatment such as with Gleevec.

In yet another aspect, the invention includes methods for predicting the FAB classification of an AML patient, the method comprising determining the level of MPO in a body fluid sample from the patient and using said MPO level to predict the FAB classification of the AML patient. In some embodiments, low MPO levels are used to indicate that the patient is M0 or M6 or elevated MPO levels indicate that the patient is not MO or M6.

The MPO level can be measured by any means known. In one embodiment, MPO is measured by immunoassay. Such assays involve the use of antibodies that recognize MPO. In certain preferred embodiments the immunoassay is one or more assays selected from the group consisting of radioimmunoassay; enzyme-linked immunosorbent assay, immunoradiometric assay, enzyme-labeled immunometric assay, fluorescent labeled immunoassay, luminescent labeled immunoassay, and immunoprecipitation assay. It is understood that levels of MPO can be determined by detecting one or more specific portions of the MPO molecule. That is, monoclonal or polyclonal antibodies raised against one or more epitopes of the MPO molecule can be used to determine the levels of MPO in the present invention.

In preferred embodiments, blood, serum or plasma are used as the body fluid sample; more preferably serum or plasma. Plasma and serum can be prepared from whole blood using suitable methods well-known in the art. When an analyte is detected in serum or plasma, the detected analyte is present in the non-cellular portion of blood. In preferred embodiments, the MPO levels are representative of a soluble free form of MPO in the plasma or serum. In these embodiments, the levels of MPO do not represent MPO that is contained within blood cells. As such, methods that detect MPO solely inside blood cells, such as myeloid blast cells, are excluded from these embodiments of the invention. For example, assays that determine the portion of blast cells, or other cells in a body fluid sample, that are positive for MPO staining, are assays that detect MPO contained within cells. Thus, in certain embodiments the present methods determine the level of myeloperoxidase in a body fluid from a mammal, wherein the determination is not by immunochemistry, cytochemistry, histochemistry, flow cytometry or other cytological or histological techniques. In certain embodiments the levels of MPO are expressed as units MPO per unit volume of the body fluid; e.g. nanograms MPO per milliliter serum or plasma.

In some embodiments, the body fluid can be processed by adding a reagent that lyses any cells present. By this approach, the MPO in cells is released into the liquid portion of the sample which also may contain MPO. Cells may be lysed by mixing the blood with a surfactant. Such surfactants can be anionic surfactants, cationic surfactants or amphoteric surfactants. Examples of anionic surfactants include sodium dodecyl sulfate, sodium dodecyl sulfonate, sodium dodecyl-N-sarcosinate, sodium cholate, sodium deoxycholate, and sodium taurodeoxycholate. Examples of cationic surfactants include hexadecyltrimethylammonium bromide, hexadecyltrimethylammonium chloride, didecyldimethylammonium chloride, didecyldimethylammonium bromide, dodecyltrimethylammonium chloride, dodecyltrimethylammonium bromide, octadecyltrimethylammonium chloride, octadecyltrimethylammonium bromide, tetradecylammonium bromide, dodecylpyridinium chloride, hexadecylpyridinium chloride, hexadecylpyridinium bromide, 1-laurylpyridinium chloride, and tetradecyltrimethylammonium bromide. Examples of amphoteric surfactants include 3-[(3-cholamidopropyl)dimethylammonio]-1-propanesulfonic acid, 3-[(3-cholamidopropyl)dimethylammonio]-2-hydroxy-1-propanesulfonic acid, palmitoyl lysolecithin, dodecyl-N-betaine, and dodecyl-β-alanine. Examples of nonionic surfactants include octyl glucoside, heptyl thioglucoside, decanoyl-N-methylglucamide, polyoxyethylene dodecyl ether, polyoxyethylene heptamethyl hexyl ether, polyoxyethylene isooctyl phenyl ether, polyoxyethylene nonyl phenyl ether, a fatty acid ester of polyoxyethylene, a fatty acid ester of sucrose, and polyoxyethylene sorbitol ester.

An MPO determination that is performed using a sample subjected to a cell lysis step may reflect MPO present outside the cells in the original sample and MPO released from the cells following lysis. In a preferred embodiment, the MPO level is determined only on the non-cellular liquid portion of the original body fluid sample. In such case, intracellular MPO would not substantially contribute to the detected MPO level. It is understood that many body fluid collection techniques may result in incidental lysis of a small portion of cells and, therefore, may release a small amount of intracellular MPO. In such case, the amount of MPO from the cells may be negligible in comparison with that present in the liquid non-cellular portion of the original sample.

The following examples serve to illustrate the present invention. These examples are in no way intended to limit the scope of the invention.

EXAMPLES

Example 1

MPO Levels in Healthy Adult Humans and Comparison of Types of Biological Samples Blood samples were obtained from 50 males and 57 females ranging in age from 18-57 years. Each of the subjects selected were apparently healthy, ambulatory, community dwelling non-medicated adults.

The following types of blood samples were taken from the subjects, (1) plasma, with EDTA as an anticoagulant, (2) plasma with heparin as an anticoagulant and (3) serum. The MPO levels of each sample were assayed by ELISA using the BIOXYTEC™ MPO Enzyme Immunoassay kit (manufactured and sold by OXIS International, Inc., U.S.A.) in accordance with manufacturer's instructions.

No statistical differences in the MPO levels were observed based on the age or sex of the subjects. The following values were established as reference ranges for MPO levels of healthy adults for each of the sampling:

| | |
|---|---|
| Plasma (EDTA) | 3.5-20.6 ng/mL |
| Plasma (Heparin) | 3.1-35.8 ng/mL |
| Serum | 4.5-44.2 ng/mL |

Example 2

MPO Levels in Normal, MDS, AML and CML Patients

Plasma (EDTA) was collected from 107 control subjects, 28 patients diagnosed with MDS, 144 patients diagnosed with AML and 107 patients diagnosed with CML. Of the 107 patients in the CML group, 74 were in the chronic phase of the disease and 33 were in the ACC/blast phase. Levels of MPO in the plasma samples were analyzed as described in Example 1.

| Group | Median | Range |
|---|---|---|
| Control | 4.9 ng/mL | 3.5 to 20.6 ng/mL |
| MDS | 13.6 ng/mL | 3.0 to 521.9 ng/mL |
| AML | 19.3 ng/mL | 1.0 to 9,514.7 ng/mL |
| CML (total) | 38.39 ng/mL | 3.39 to 11,421.6 ng/mL |
| CML (chronic phase only) | 38.22 ng/mL | 4.48 to 11,421.6 ng/mL |
| CML (ACC/blast phase only) | 47.00 ng/mL | 9.93 to 1,423.6 ng/mL |

The patients with MDS, AML or CML had significantly higher plasma MPO levels than control subjects. Also, the plasma MPO levels of CML patients were significantly higher than MDS and AML patients. There were no significant differences between MDS and AML patients. There were no significant differences in the MPO levels between CML patients in the chronic phase and CML patients in the ACC/blast phase. FIG. 1 shows the distribution of MPO levels in CML patients.

Example 3

Correlation Between Plasma Levels of MPO and Prognosis of AML and MDS Patients

Plasma (EDTA) was collected from AML and MDS patients (172 total patients: 144 AML and 28 MDS), and MPO levels were determined as described in example 1. All samples were collected from patients that had not previously received treatment for the hematological disorder. The patients were treated within 24-48 hours and the medical status of the patients (i.e. survival, remission rate and remission duration) were followed for a period ranging from a few days to 149 weeks, with a median of 21 weeks. The MPO levels of the patients were subsequently correlated to survival time (in weeks). Because MPO levels and overall survival did not differ significantly between MDS and AML patients, the two groups were considered together for subsequent analyses. Ninety percent of AML patients die within 2 years following diagnosis.

Cox regression model showed that MDS and AML patients with higher MPO levels have significantly shorter survival in continuous fashion (P<0.001) compared with patients with lower MPO levels (see table below). MPO levels that were higher by 1 ng/mL correlated to shorter overall survival times.

Multivariate analysis showed that the correlation between increased levels of MPO and shorter survival was irrespective of other important prognostic factors, including cytogenetics, performance status, AHD (antecedent hematological disease), age, or diagnosis (MDS v. AML). When AML patients were considered alone (independent of MDS patients), Cox regression analysis also revealed a significant inverse correlation between MPO levels and overall survival. Thus, MPO level is an independent prognostic factor in MDS and AML patients and may be combined with other factors such as cytogenetics, performance status, AHD (antecedent hematological disease), age, and diagnosis (MDS v. AML) for increased prognostic power.

patients that achieved complete response to treatment, the length of time to relapse (complete remission duration; CRD) was determined and correlated to the MPO levels. The CRD of the patients in the study varied from 2 weeks to 146 weeks (median, 24.5 weeks).

Figure 2:
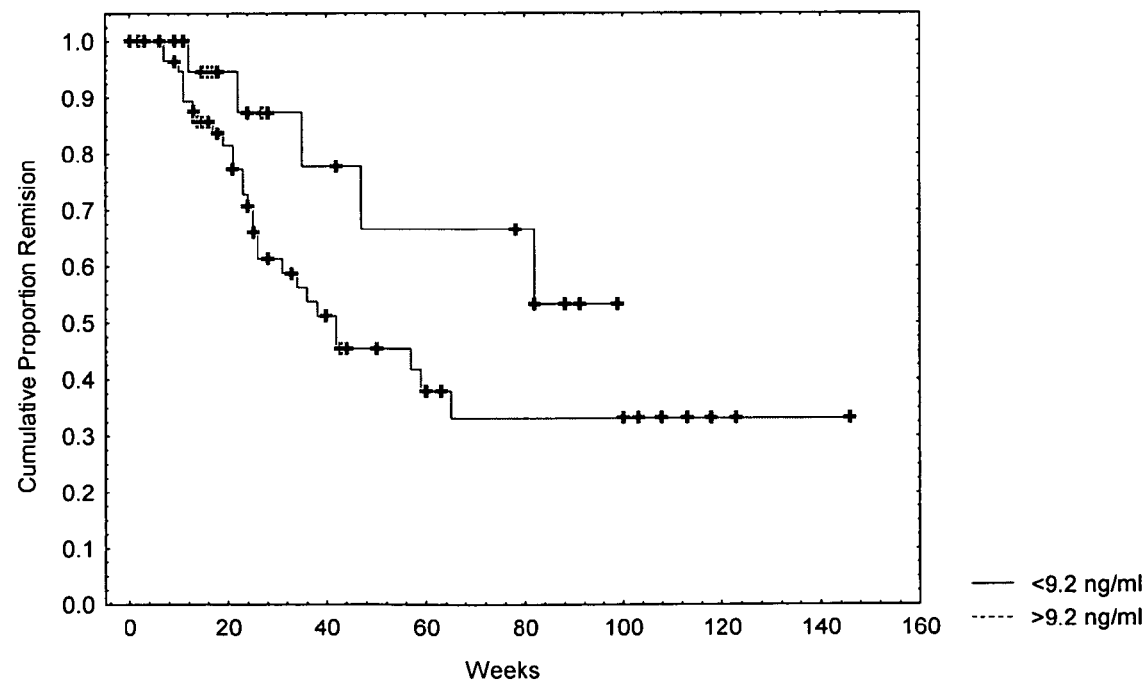
FIG. 2 shows the complete remission duration (CRD) of MDS and AML patients expressed as the cumulative proportion remission at specific time points, with MPO levels of 9.2 ng/mL used as a threshold value.

MDS and AML patients that were responders to treatment and that had high MPO levels (>9.2 ng/mL) exhibited shorter complete remission duration periods (P=0.07). FIG. 2 shows the complete remission duration of MDS and AML patients expressed as the cumulative proportion of patients surviving at specific time points, with MPO levels of 9.2 ng/mL used as a threshold value. As can be seen, MDS and AML patients Statistical Significance of Correlations Between MPO Levels and Survival in MDS and AML Patients Cox regression model (univariate)

|  | Beta | Standard Error | t-value | Exponent Beta | Wald Statist. | p |
|---|---|---|---|---|---|---|
| MPO | .0004 | .0001 | 3.3260 | 1.0004 | 11.06232 | 000882 |

Multivariate models:

|  | Beta | Standard Error | t-value | Exponent Beta | Wald Statist. | p |
|---|---|---|---|---|---|---|
| MPO | .0004 | .000133 | 3.168117 | 1.000420 | 10.03697 | .001536 |
| Cytogenetic. | 198 | .047603 | 4.178473 | 1.220070 | 17.45964 | .000029 |

|  | Beta | Standard Error | t-value | Exponent Beta | Wald Statist. | p |
|---|---|---|---|---|---|---|
| MPO | .000388 | .000131 | 2.969774 | 1.000388 | 8.81956 | .002982 |
| AGE | .030353 | .009619 | 3.155600 | 1.030819 | 9.95781 | .001603 |
| Cytoge | .156725 | .046859 | 3.344608 | 1.169675 | 11.18640 | .000825 |
| PS_ | .231079 | .288501 | .800967 | 1.259959 | .64155 | .423157 |
| AHD | .003855 | .001745 | 2.209273 | 1.003862 | 4.88089 | .027163 |
| GDX | −.071861 | .340605 | −.210981 | .930660 | .04451 | .832903 |

Statistical Significance of Correlations Between MPO Levels and Survival in AML Patients Only Cox regression model (univariate)

|  | Beta | Standard Error | t-value | Exponent Beta | Wald Statist. | p |
|---|---|---|---|---|---|---|
| MPO | .000421 | .000134 | 3.139467 | 1.000421 | 9.856255 | .001694 |

Multivariate models:

|  | Beta | Standard Error | t-value | Exponent Beta | Wald Statist. | p |
|---|---|---|---|---|---|---|
| MPO | .000351 | .000131 | 2.682626 | 1.000351 | 7.19649 | .007308 |
| Cytoge | 1.383171 | .240109 | 5.760591 | 3.987525 | 33.18441 | .000000 |

Example 4

Correlation Between Plasma MPO Levels and Complete Remission Duration of MDS and AML Patients Undergoing Treatment Plasma was collected from 90 patients diagnosed with AML or MDS and MPO levels were determined as described in example 1. Plasma samples were collected from the patients before therapy was administered. The medical status of the patients were then followed to determine response to cytosine arabinoside (ara-C) with idarubicin treatment. In with MPO levels lower than 9.2 ng/mL tended to live longer than patients with MPO values higher than 9.2 ng/mL.

Example 5

Correlation Between Plasma MPO Levels of CML Patients and Responsiveness to Gleevec Treatment Plasma (EDTA) was collected from 104 CML patients undergoing Gleevec treatment and MPO levels were determined as described in example 1. The medical status of the patients was then followed for a median period of 21.3 months. The MPO levels were compared with the incidence of the patients responding or not responding to the Gleevec treatment.

Figure 3:
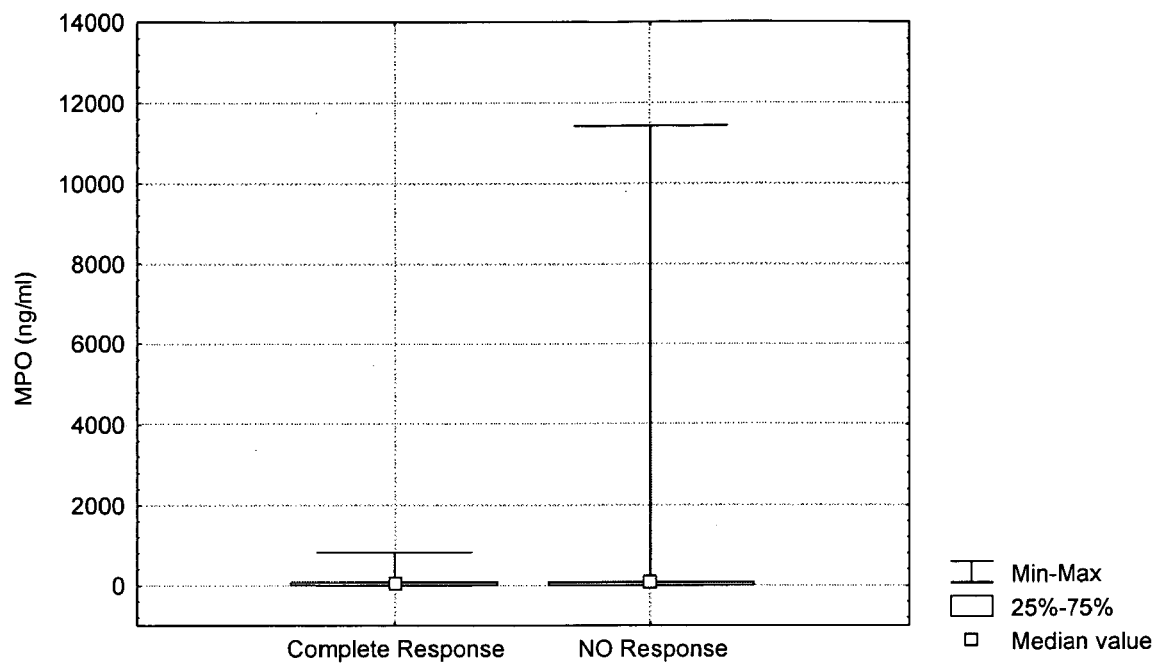
FIG. 3 shows the levels of MPO in CML patients in the chronic and ACC/BC stages in relation to responders vs. non-responders.
Figure 4:
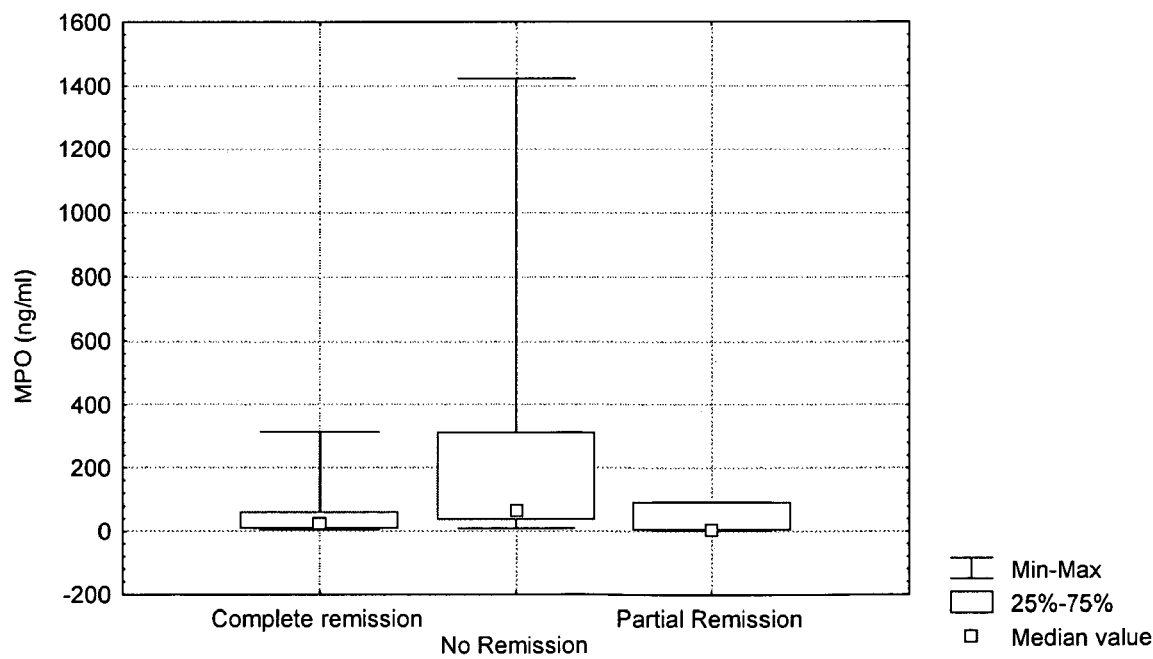
FIG. 4 shows the levels of MPO in CML patients in the ACC/BC stage in relation to responders vs. non-responders.

The CML patients that responded to Gleevec treatment had significantly (P=0.03) lower MPO levels than non-responders (FIG. 3). When CML patients in the ACC/blast phase (a total of 33 patients) were considered independently of the chronic phase CML patients, there was also a significant (P=0.04) correlation between MPO levels and response to Gleevec treatment, with responders having significantly lower levels of MPO than non-responders (FIG. 4).

Example 6

Figure 5:
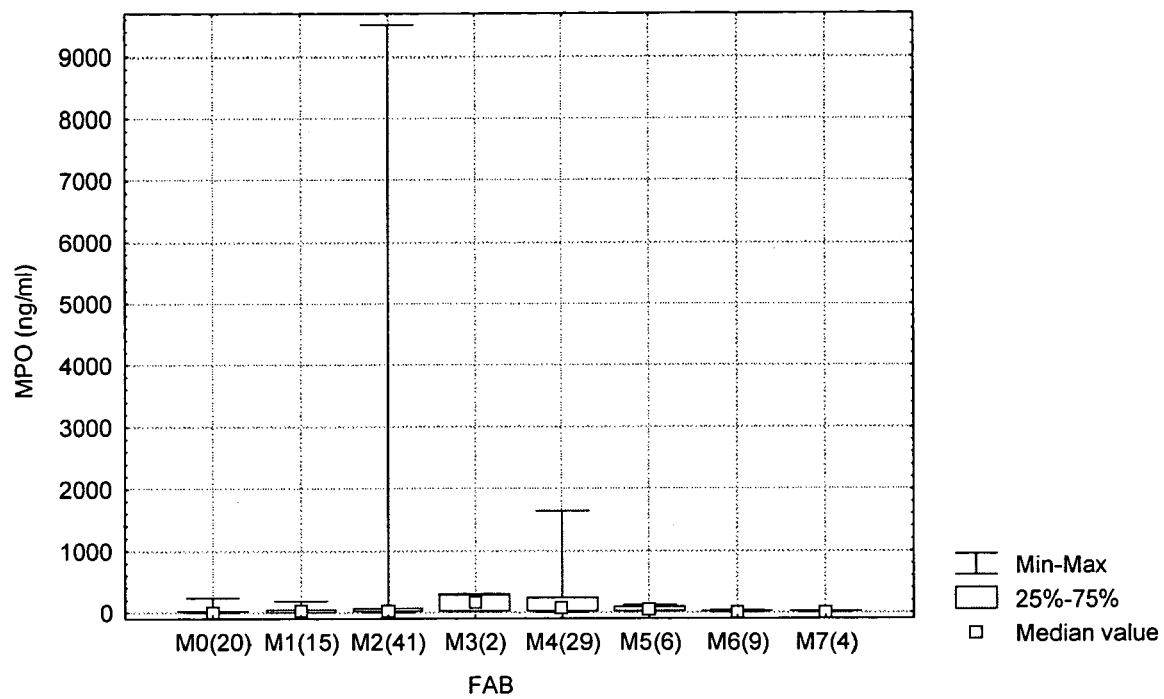
FIG. 5 shows the levels of MPO in AML patients in relation to the FAB classification of the patients.

Correlation Between Differentiation of Leukemic Cells and Plasma MPO Levels in AML Patients 129 AML patients were subdivided based on the levels of differentiation of leukemic cells according to the FAB classification as follows: 29 patients were M0, 15 patients were M1, 41 patients were M2, 2 patients were M3, 29 patients were M4, 6 patients were M5, 9 patients were M6 and 4 patients were M7. Plasma was collected from each patient and MPO levels were determined as described in Example 1. The MPO levels of the patient were compared with the FAB classification of the patients (FIG. 5).

AML patients classified as M0 and M6 had significantly (P=0.0001) lower MPO levels than patients classified as M2, M3 and M4.

Example 7

Correlation Between MPO and Other Physiological Hemotologic Markers in MDS and AML Patients There is a positive correlation between MPO levels and white blood cells (WBC), beta-2 microglobulin (B2M), monocytes, lactate dehydrogenase (LDH), blood urea nitrogen (BUN), and creatin (CREAT) in patients diagnosed with MDS or AML. Thus, one can combine MPO levels with one or more of these other prognostic factors to achieve more accurate diagnosis or prognosis.

| Spearman Rank Order Correlations In MDS and AML Patients | | | |
|---|---|---|---|
| | Valid N | Spearman R | t(N-2) | p-level |
| MPO & AGE | 172 | .027094 | .35339 | .724232 |
| MPO & AHD_ | 169 | −.070791 | −.91712 | .360403 |
| MPO & B2M | 162 | .315557 | 4.20644 | .000043 |
| MPO & WBC | 172 | .310582 | 4.26017 | .000034 |
| MPO & BL_BL | 172 | .151951 | 2.00447 | .046607 |
| MPO & BL_MON | 172 | .376974 | 5.30664 | .000000 |
| MPO & BL_LYM | 172 | −.185708 | −2.46420 | .014727 |
| MPO & ABS_LYM | 64 | .232485 | 1.88216 | .064510 |
| MPO & PLT | 172 | −.090950 | −1.19078 | .235399 |
| MPO & HGB | 171 | .116833 | 1.52930 | .128059 |
| MPO & BM_BLA | 172 | .006737 | .08784 | .930107 |
| MPO & BM_MO | 172 | .351710 | 4.89873 | .000002 |
| MPO & BM_LYM | 172 | −.176722 | −2.34101 | .020392 |
| MPO & BUN | 172 | .185189 | 2.45707 | .015012 |
| MPO & CREAT | 172 | .179681 | 2.38152 | .018347 |
| MPO & LDH | 172 | .211423 | 2.82027 | .005368 |
| MPO & CD13 | 155 | .174635 | 2.19383 | .029756 |
| MPO & CD33 | 156 | −.000723 | −.00897 | .992857 |
| MPO & CD34 | 156 | −.045422 | −.56426 | .573398 |
| MPO & CD64 | 155 | .183753 | 2.31227 | .022096 |

Example 8

Correlation Between MPO and Other Physiological Hemotologic Markers in CML Patients There is a remarkable correlation between MPO and WBC, LDH, % basophiles, and % of Ph+ metaphases. Thus, one can combine MPO levels with one or more of these other prognostic factors to achieve more accurate diagnosis or prognosis.

| Spearman Rank Order Correlations In CML Patients | | | |
|---|---|---|---|
| | Valid N | Spearman R | t(N-2) | p-level |
| MPO & HGB_AI_ | 74 | −.074314 | −.63232 | .529181 |
| MPO & PLT_AI_ | 74 | .191450 | 1.65512 | .102252 |
| MPO & WBC_AI_ | 74 | .733929 | 9.16865 | .000000 |
| MPO & BL_AI_ | 45 | .260917 | 1.77234 | .083424 |
| MPO & PRO_AI_ | 46 | .218030 | 1.48190 | .145494 |
| MPO & M_M_AI_ | 60 | .483665 | 4.20847 | .000090 |
| MPO & POLY_AI | 74 | −.048086 | −.40850 | .684122 |
| MPO & LYMPH_ | 74 | −.589181 | −6.18733 | .000000 |
| MPO & EOS_AI_ | 64 | −.142908 | −1.13693 | .259943 |
| MPO & BASO_A_ | 74 | .265083 | 2.33275 | .022460 |
| MPO & MONO_I_ | 72 | −.065962 | −.55308 | .581968 |
| MPO & NRBC_I_ | 60 | .317991 | 2.55433 | .013288 |
| MPO & ALB_AI_ | 73 | .242523 | 2.10643 | .038703 |
| MPO & CREATAI | 74 | .056437 | .47964 | .632934 |
| MPO & BILI_AI_ | 74 | −.107253 | −.91535 | .363062 |
| MPO & NLDH_I_ | 74 | .680292 | 7.87576 | .000000 |
| MPO & SGOT_I_ | 62 | .246238 | 1.96795 | .053701 |
| MPO & CELLUR | 54 | .283963 | 2.13560 | .037441 |
| MPO & BLASTS | 73 | .120187 | 1.02011 | .311141 |
| MPO & CYTO_T | 74 | −.127608 | −1.09171 | .278599 |
| MPO & PRE_% PH | 74 | .570716 | 5.89747 | .000000 |
| MPO & PREFISH | 30 | .136004 | .72642 | .473612 |
| MPO & PREPCR | 19 | .012302 | .05073 | .960134 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method for determining a prognosis of an individual with AML (acute myeloid leukemia), said method comprising determining a level of myeloperoxidase in a body fluid sample from said individual, providing said level to a medical practitioner, and correlating said level to a predicted clinical outcome for the disease;
   wherein said prognosis is complete remission duration (CRD) and wherein a myeloperoxidase level greater than about 9.2 ng/mL is indicative of a shorter complete remission duration and a myeloperoxidase level lower than 9.2 ng/mL is indicative of a longer CRD.

2. The method of claim 1, wherein said body fluid sample does not contain cells.

3. The method of claim 1, wherein said method does not include a step of lysing any cells present in the body fluid sample.

4. The method according to claim 1, wherein the determination of a myeloperoxidase level is performed using an immunoassay.

5. The method according to claim 1, wherein the determination of a myeloperoxidase level is performed using an assay is selected from the group consisting of radioimmunoassay; enzyme-linked immunosorbent assay, immunoradiometric assay, enzyme-labeled immunometric assay, fluorescent labeled immunoassay, luminescent labeled immunoassay, and immunoprecipitation assay.

6. The method according to claim 1, wherein said body fluid is selected from the group consisting of blood, serum or plasma.

7. The method according to claim 1, wherein said mammal is a human.

8. A method for determining a prognosis of an individual with AML (acute myeloid leukemia), said method consisting essentially of determining a level of myeloperoxidase in a body fluid sample from said individual, providing said level to a medical practitioner, and correlating said level to a predicted clinical outcome for the disease;
   wherein said prognosis is complete remission duration (CRD) and wherein a myeloperoxidase level greater than about 9.2 ng/mL is indicative of a shorter complete remission duration and a myeloperoxidase level lower than 9.2 ng/mL is indicative of a longer CRD.

9. The method of claim 8, wherein said body fluid sample does not contain cells.

10. The method of claim 8, wherein said method does not include a step of lysing any cells present in the body fluid sample.

11. The method according to claim 8, wherein the determination of a myeloperoxidase level is performed using an immunoassay.

12. The method according to claim 8, wherein the determination of a myeloperoxidase level is performed using an assay is selected from the group consisting of radioimmunoassay; enzyme-linked immunosorbent assay, immunoradiometric assay, enzyme-labeled immunoinetric assay, fluorescent labeled immunoassay, luminescent labeled immunoassay, and immunoprecipitation assay.

13. The method according to claim 8, wherein said body fluid is selected from the group consisting of blood, serum or plasma.

14. The method according to claim 8, wherein said mammal is a human.

* * * * *

UNITED STATES PATENT AND TRADEMARK OFFICE
CERTIFICATE OF CORRECTION

PATENT NO.       : 7,569,353 B2                                        Page 1 of 1
APPLICATION NO.  : 10/982534
DATED            : August 4, 2009
INVENTOR(S)      : Maher Albitar It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 333 days.

Signed and Sealed this

Seventh Day of September, 2010

David J. Kappos
*Director of the United States Patent and Trademark Office*